United States Patent [19]
Okashita et al.

[11] Patent Number: 6,082,859
[45] Date of Patent: Jul. 4, 2000

[54] OPHTHALMOLOGICAL PHOTOGRAPHING APPARATUS

[75] Inventors: Toshihiro Okashita; Hiroyuki Ohtsuka; Takeyuki Kato, all of Tokyo, Japan

[73] Assignee: Kabushiki Kaisha TOPCON, Tokyo, Japan

[21] Appl. No.: 09/297,083

[22] PCT Filed: Sep. 17, 1998

[86] PCT No.: PCT/JP98/04196

§ 371 Date: May 17, 1999

§ 102(e) Date: May 17, 1999

[87] PCT Pub. No.: WO99/13763

PCT Pub. Date: Mar. 25, 1999

[30] Foreign Application Priority Data

Sep. 17, 1997 [JP] Japan .................................. 9-251221

[51] Int. Cl.⁷ .......................................... A61B 3/14
[52] U.S. Cl. ............................................... 351/206
[58] Field of Search .................................... 351/205, 206, 351/207, 211, 212, 214, 221, 245, 246; 356/346, 326, 395, 396

[56] References Cited

U.S. PATENT DOCUMENTS 5,159,361  10/1992  Cambier et al. ...................... 351/212
5,784,162  10/1992  Cabib et al. .......................... 356/346

FOREIGN PATENT DOCUMENTS

| 59-93401 | 6/1984 | Japan . |
| 63-5725 | 1/1988 | Japan . |
| 4-317629 | 11/1992 | Japan . |
| 5-285104 | 11/1993 | Japan . |
| 7-178057 | 7/1995 | Japan . |

*Primary Examiner*—George Manuel
*Attorney, Agent, or Firm*—Jacobson, Price, Holman & Stern, PLLC

[57] ABSTRACT

A photographic instrument for ophthalmology permits easily recognizing which portion of an eye E to be examined a position of a photographed portion of the eye E corresponds to. The instrument comprises a display means 8 for displaying a portion to be photographed as a part of the entire eye E as an alignment image when the eye E is photographed and for displaying a recognition pattern for recognizing the position of the portion to be photographed.

10 Claims, 11 Drawing Sheets

OPHTHALMOLOGICAL PHOTOGRAPHING APPARATUS

DETAILED DESCRIPTION OF THE INVENTION

1. Field of Use in the Industry

The present invention relates to an improvement of a photographic instrument for ophthalmology for photographing various portions of an eye to be examined, such as its fundus, corneal endothelium, and cornea cross section.

2. Prior Art

A photographic instrument for ophthalmology for photographing various portions of an eye to be examined, such as its fundus, corneal endothelium and cornea cross section has heretofore been known. In a photographic instrument for ophthalmology of this type, e.g., a fundus camera for photographing the fundus of the eye, a portion of the fundus to be photographed, as a part of the entire fundus, is displayed on a monitor screen as an alignment image, and then the portion is photographed. After that, the photographed portion is recorded in, for example, a still video recorder as a recording means.

In the fundus photography of this type, sometimes performed is a so-called "panoramic photography" in which different portions of a fundus are photographed, respectively, to obtain a plurality of photographed portions, thereby obtaining the entire image of the fundus.

The Problems to be Solved by the Invention:

In the panoramic photography of this type, a plurality of photographs with a low magnification are taken. Since an examiner chooses eye fixation by his own will and photographs the portions of the fundus to be photographed, some portions may fail to be photographed. Also, if a plurality of photographed portions are recorded and preserved separately, it is not easy to find later which photographed portion represents which portion of the entire fundus. Therefore, the panoramic photography is inconvenient for the prompt diagnosis and image analysis with the aid of the photographed images. Under the circumstances, it is desirable in term of the picture image supervision to recognize the different photographed sites of the fundus together with their mutual relations.

The object of the present invention, which has been achieved in view of the situation described above, is to provide a photographic instrument for ophthalmology capable of easily recognizing which portion of an eye to be examined each of the positions of portions to be photographed and photographed portions corresponds to.

Means for Solving the Problem:

A photographic instrument for ophthalmology as defined in claim 1 comprises display means for displaying portions to be photographed each as a part of an entire of an eye to be examined as alignment images together with a recognition pattern for recognizing positions of the portions to be photographed relative to the entire of the eye to be examined when the eye to be examined is photographed.

A photographic instrument for ophthalmology as defined in claim 2 is characterized in that a plurality of combinations of numbers and sites of the portions are previously stored in memory means of the photographic instrument for ophthalmology and the numbers and sites can be arbitrarily selected from among the stored combinations.

A photographic instrument for ophthalmology as defined in claim 3 is characterized in that the recognition pattern is displayed so that a portion that has been photographed can be distinguished from a portion that has not been photographed yet.

A photographic instrument for ophthalmology as defined in claim 4 is characterized in that a portion that is to be photographed in a next step is displayed in the recognition pattern.

A photographic instrument for ophthalmology as defined in claim 5 is characterized in that the recognition pattern is displayed as another pattern when the same portion is photographed again.

A photographic instrument for ophthalmology as defined in claim 6 is characterized in that the recognition pattern displays a number of photographs to make it possible to know the number of photographs of a portion that has been photographed.

A photographic instrument for ophthalmology as defined in claim 7 comprises display means for displaying a recognition pattern for permitting a position of a photographed portion to be recognized relative to the entire of an eye to be examined when the eye is photographed or after the eye is photographed; and recording means for recording an image of the photographed portion as well as positional information on the photographed portion that indicates the position of the photographed portion relative to an entire of a fundus while allowing the image of the photographed portion to be related to the entire of the fundus by designating a position in the recognition pattern displayed on a screen.

A photographic instrument for ophthalmology as defined in claim 8 is characterized in that the photographing portion of the eye to be examined is its fundus, corneal endothelium or cornea cross section.

A photographic instrument for ophthalmology as defined in claim 9 is characterized in that the photographed portion of an eye to be examined is its fundus and the recognition pattern is either a fundus image or a schematic fundus image.

A photographic instrument for ophthalmology as defined in claim 10 is characterized in that, when a portion to be photographed is displayed in a way of a panoramic display, each partial image is displayed on a screen in a manner to correspond to information on an eye fixing position.

Function:

According to the present invention, it is possible to easily recognize which portion of an eye to be examined each of the positions of portions to be photographed and photographed portions corresponds to.

BRIEF DESCRIPTION OF THE DRAWINGS

FIG. 8 exemplifies a case where a fundus portion recorded in recording means is read out to be displayed on a screen, wherein FIG. 8(a) is an explanatory view showing a state to designate a partial image displayed on the screen for displaying its magnified image on the screen, and FIG. 8(b) is an explanatory view showing a process for joining the magnified images displayed on the screen to form a panoramic image;

FIG. 9 exemplifies another case where the fundus portion recorded in the recording means is read out to be displayed on the screen, wherein FIG. 9(a) is an explanatory view showing a state to designate a partial image displayed on the screen for displaying its magnified image on the screen, and FIG. 9(b) is an explanatory view showing a process for joining the magnified images displayed on the screen to form a panoramic image;

FIG. 10 exemplifies another recognition pattern displayed on a screen, wherein FIG. 10(a) covers a case where square meshes of the recognition pattern are arranged vertically and horizontally to form a cross (+) configuration, FIG. 10(b) covers a case where nine square meshes are arranged to form a square configuration (3 meshes×3 meshes) and an additional square mesh is added to the central mesh at each of the four sides of the square configuration to form a recognition pattern, FIG. 10(c) covers a case where a square mesh is arbitrarily designated from among a recognition pattern consisting of 64 square meshes (8 meshes×8 meshes) and eight fundus portions around the designated square mesh can be photographed, and FIG. 10(d) shows the fundus portions corresponding to the recognition pattern shown in FIG. 10(a);

FIG. 12 is an explanatory view showing a second embodiment of the present invention, wherein FIG. 12(a) shows a state that a portion to be photographed in the vicinity of a papilla is displayed as an alignment image and a recognition pattern is also displayed, FIG. 12(b) shows a state that a portion to be photographed at an immediately rightward position of the photographed portion in the vicinity of the papilla is displayed as an alignment image and a recognition pattern is also displayed, and FIG. 12(c) shows a state that photographed portions photographed by an external fixation lamp are superimposed to be displayed.

EMBODIMENTS

Embodiment 1

Figure 1:
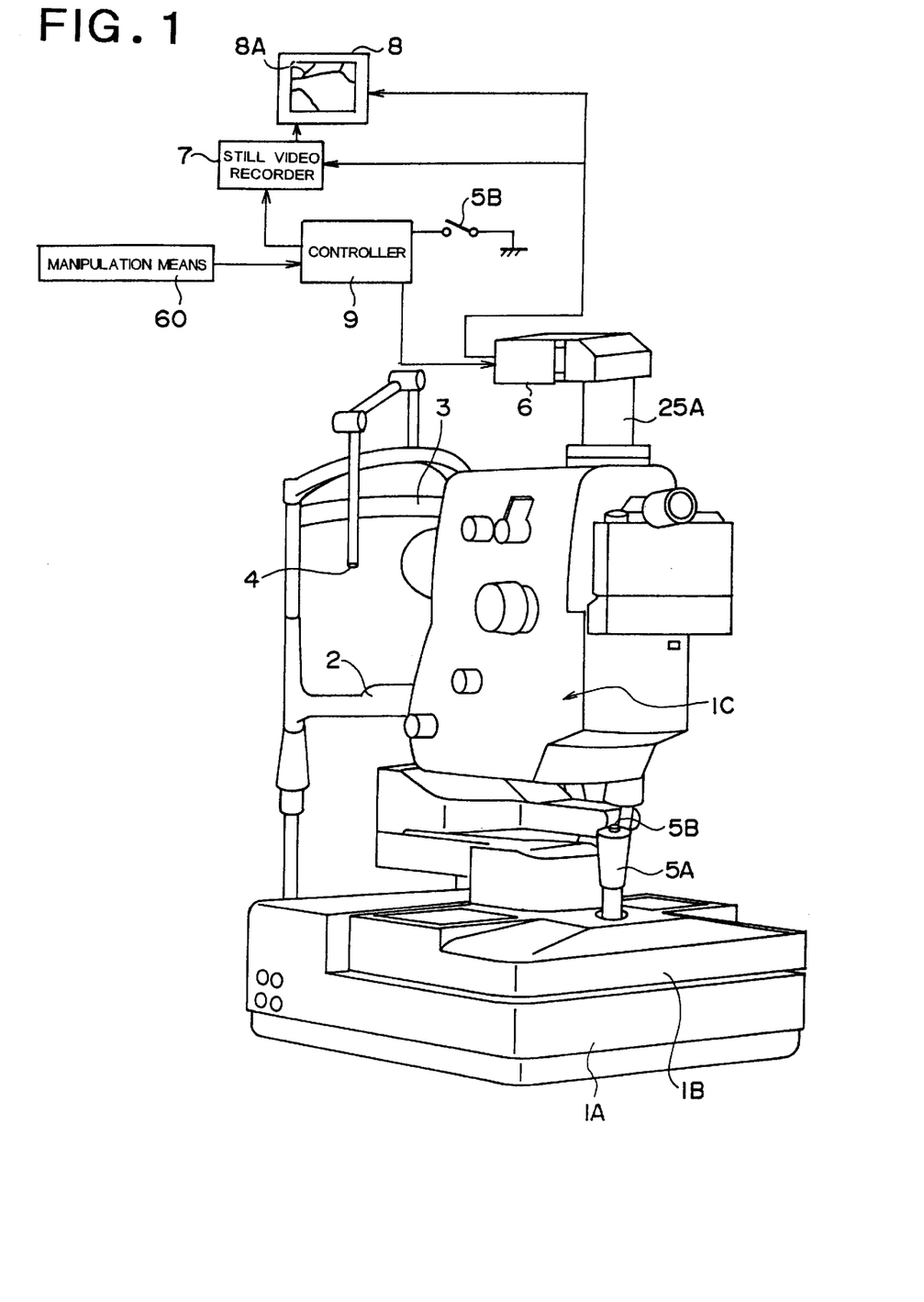
FIG. 1 shows an outer appearance of a photographic instrument for ophthalmology according to the present invention.

FIG. 1 shows an outer appearance of a fundus camera exemplifying a photographic instrument for ophthalmology of the present invention. In FIG. 1, reference numeral 1A denotes a base, reference numeral 1B denotes a rest, reference numeral 1C denotes an instrument body, reference numeral 2 denotes a chin rest, reference numeral 3 denotes a forehead rest, reference numeral 4 denotes an external eye fixation lamp, reference numeral 5A denotes a joystick, reference numeral 5B denotes a photographing switch, and reference numeral 6 denotes a TV camera. These constructions are known to a skilled person in the art. The TV camera 6 is connected to a still video recorder 7 used as an image recording instrument, and the still video recorder 7 is connected to a monitor 8. The monitor 8 displays a portion to be photographed as an alignment image on its screen 8A, which portion is a part of the entire fundus of an eye to be photographed, when the fundus is photographed. The monitor 8 also displays an image of a photographed portion that is recorded in the still video recorder 7. The monitor 8 and the still video recorder 7 are controlled by a controller 9, and the detail of the controlling of the controller 9 will be described herein later.

Figure 2:
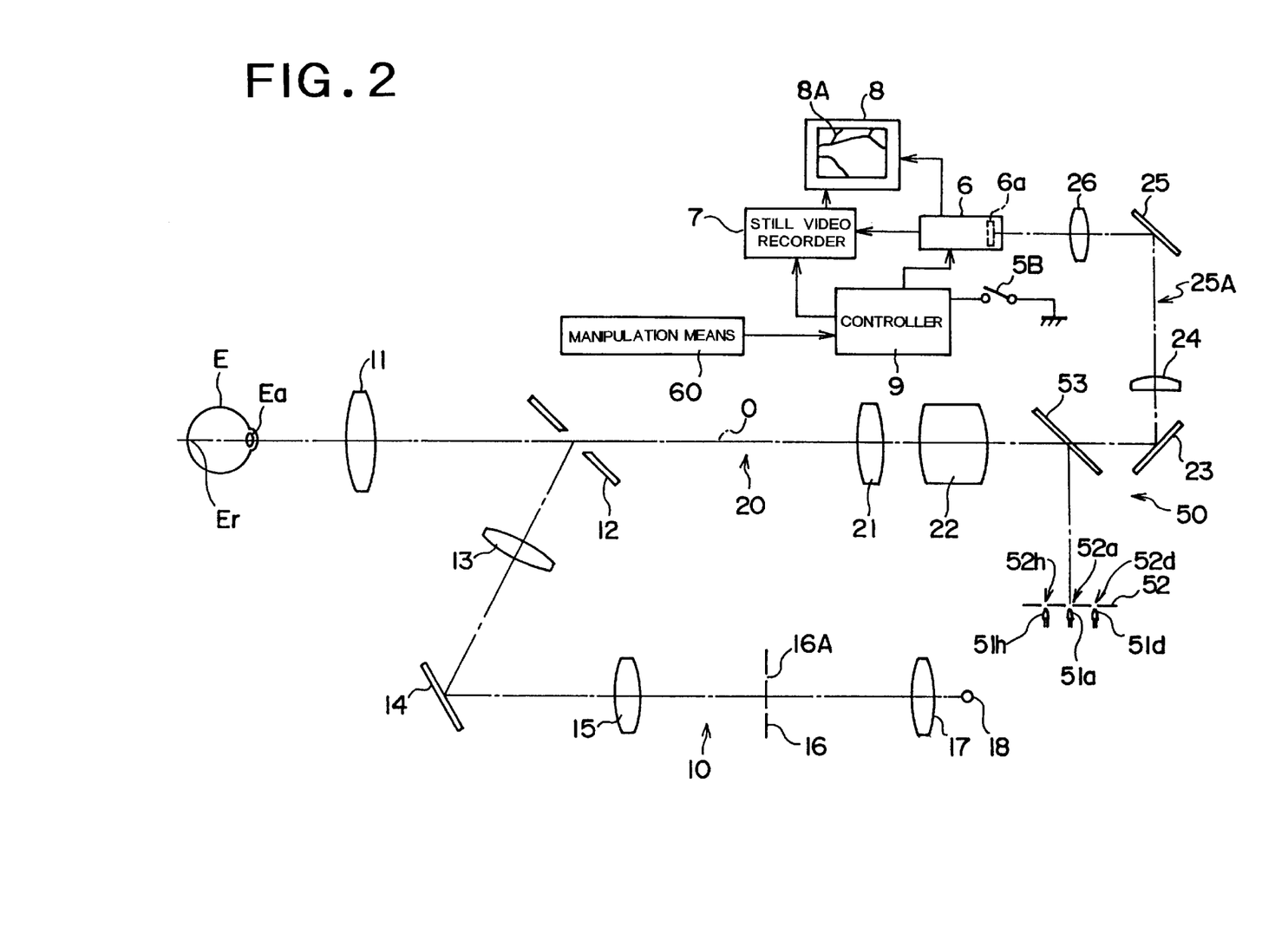
FIG. 2 shows an optical system of the photographic instrument for ophthalmology according to the present invention.

As shown in FIG. 2, the instrument body is equipped with an illuminating optical system 10 for illuminating a fundus Er of an eye E to be examined, a photographing optical system 20 for photographing the fundus Er, an inner fixation target projecting optical system 50 for projecting a fixation target onto the fundus Er to make the eye to be examined gaze at it, and an alignment optical system (not shown) for adjusting the position of instrument body in relation to the eye to be examined.

The illuminating optical system 10 includes an objective lens 11, a perforated mirror 12, a relay lens 13, a reflection mirror 14, a relay lens 15, a ring opening plate 16 having a ring opening 16A held in a conjugated relationship with the pupil Ea of the eye E to be examined, a condenser lens 17 and an illuminating light source 18.

The photographing optical system 20 includes an objective lens 11, a focusing lens 21, an image forming lens 22 and a reflection mirror 23. The TV camera 6 includes an image pickup element 6a. The TV camera 6 is optically connected to the photographing optical system 20 through a relay lens system 25A composed of a field lens 24, a reflection mirror 25 and a relay lens 26. The image pickup element 6a is maintained in an optically conjugated relationship with the fundus Er.

Figure 3:
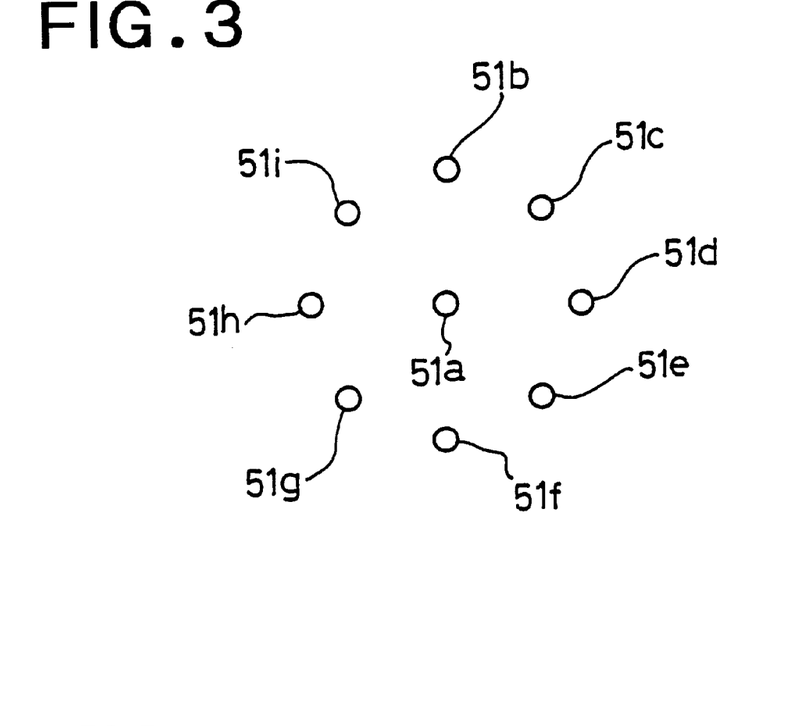
FIG. 3 shows the state of an arrangement of light-emitting diodes shown in FIG. 2.
Figure 4:
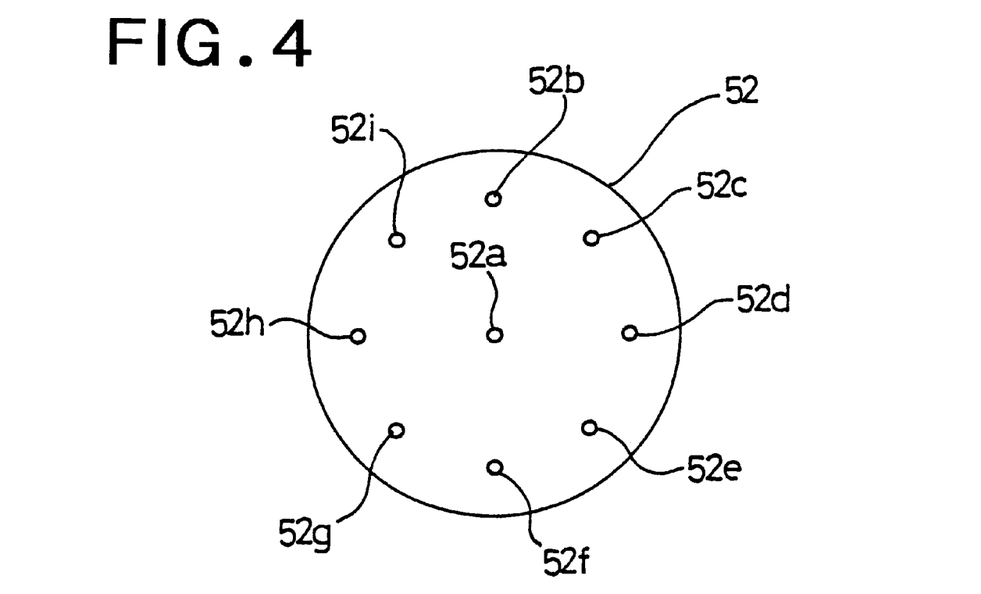
FIG. 4 is a plan view of a mask plate shown in FIG. 2.

The fixation target projecting optical system 50 includes a light-emitting diode 51a arranged in the center, eight light-emitting diodes 51b to 51i equidistantly arranged around the light-emitting diode 51a, as shown in FIG. 3, a mask plate 52 having pin holes 52a to 52i positioned so as to respectively face the light-emitting diodes 51a to 51i, as shown in FIG. 4, a half mirror 53, the image forming lens 22, the focusing lens 21 and the objective lens 11. The light emitted from these light-emitting diodes 51a to 51i is projected as a fixation target on the fundus Er through the pin holes 52a to 52i, the half mirror 53, the image forming lens 22, the focusing lens 21 and the objective lens 11 to form a pin hole image on the fundus Er. The examinee visually recognizes the fixation target so as to fix the eye fixation. The direction of the examinee's eye fixation relative to an optical axis O of the photographing optical system 20 is switched by lighting any of these pin holes 52a to 52i so as to change the portion of the fundus Er to be photographed.

Figure 5:
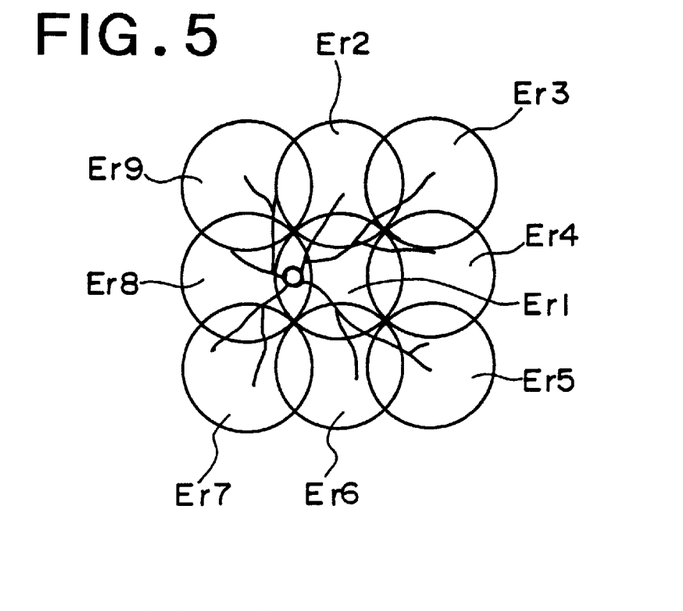
FIG. 5 shows partitioned portions of the fundus of an eye to be photographed.

In this embodiment, nine portions of the fundus Er are photographed as shown in FIG. 5. If the light-emitting diode 51a is lit, the central portion Er1 to be photographed is photographed. If the light-emitting diode 51b is lit, the portion Er2 to be photographed just above the portion Er1 is photographed. If the light-emitting diode 51c is lit, the obliquely upper portion Er3 to be photographed on the right side is photographed. If the light-emitting diode 51d is lit, the portion Er4 to be photographed on the right side is photographed. If the light-emitting diode 51e is lit, the obliquely lower portion Er5 to be photographed on the right side is photographed. If the light-emitting diode 51f is lit, the portion Er6 to be photographed just below the portion Er1 is photographed. If the light-emitting diode 51g is lit, the obliquely lower portion Er7 to be photographed on the left side is photographed. If the light-emitting diode 51h is lit, the portion Er8 to be photographed on the left side is photographed. Further, if the light-emitting diode 51i is lit, the obliquely upper portion Er9 to be photographed on the left side is photographed.

Figure 6:
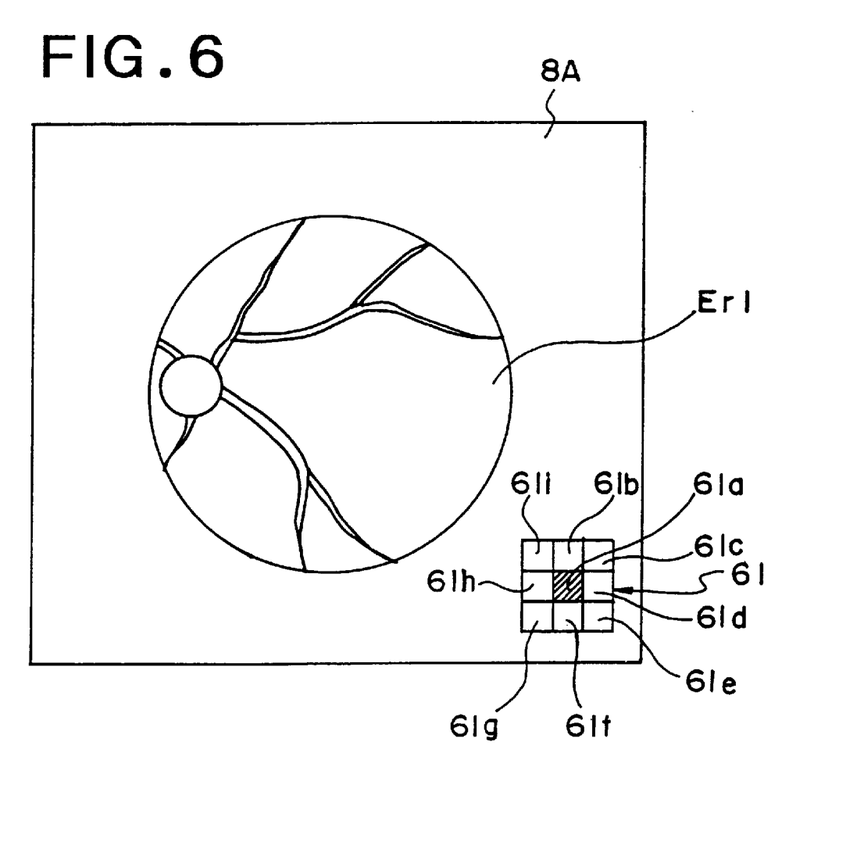
FIG. 6 is an explanatory view showing an alignment image displayed on a monitor screen and a recognition pattern, which shows the state that a central fundus portion is displayed as the alignment image.

Before photographing, the a portion to be photographed as a part of the entire fundus Er is displayed as an alignment image on the screen 8A of the monitor 8, as shown in FIG. 6. In FIG. 6, the portion Er1 is displayed on the screen 8A on the supposition that the eye to be examined gazes at the light-emitting diode 51a. The control unit 9 has a manipulation means 60 such as a mouse. By manipulating the manipulation means, a recognition pattern 61 for recognizing the position of the portion to be photographed relative to the entire fundus Er is also displayed on the screen 8A together with the alignment image.

Figure 7:
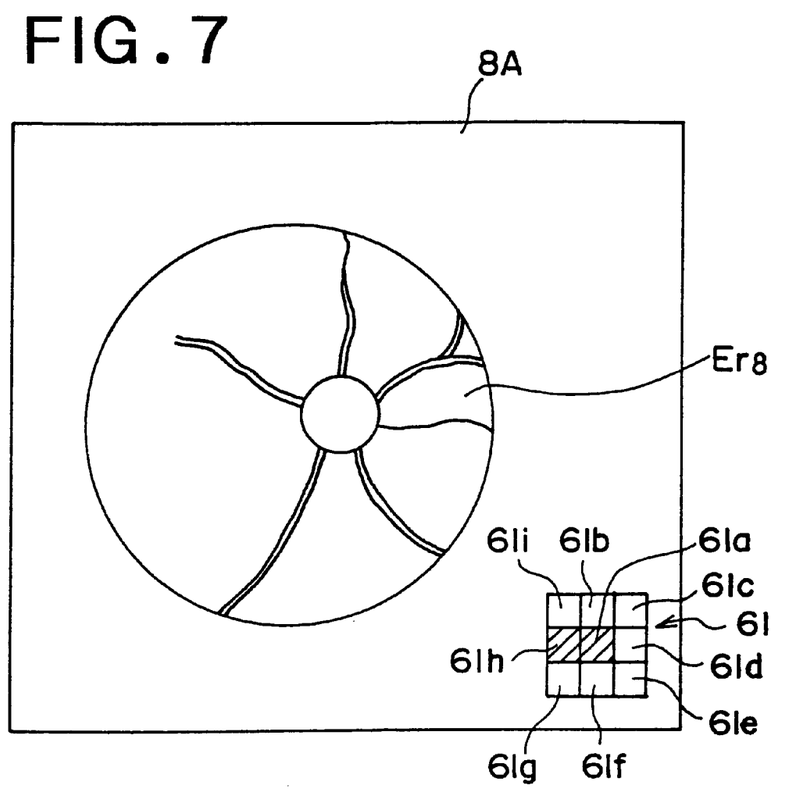
FIG. 7 is an explanatory view showing an alignment image displayed on a monitor screen and a recognition pattern, which shows the state that a fundus portion on the left side of the central fundus portion is displayed as the alignment image.

In this embodiment, the recognition pattern 61 consists of nine meshes 61a to 61i. These nine meshes 61a to 61i are arranged to be positioned correspondingly to the portions Er1 to Er9, respectively. The recognition pattern 61 is constructed so that if, for example, a portion is photographed, the brightness of the mesh corresponding to the photographed portion is increased. When photographing is not carried out at all, the brightness of each of the meshes 61a to 61i is low. If photographing is carried out by manipulating the photographing switch 5B under the state that the alignment image of the central portion Er1 is displayed, the mesh 61a is changed from the low brightness to the high brightness. As a result, it is possible to recognize which one of the portions of the entire fundus Er has been photographed. The photographed portion Er1 is recorded in the still video recorder 7. Then, if the light-emitting diode 51h is lit to guide the eye fixation of the eye E to be examined, the alignment image corresponding to the portion Er8 is displayed on the screen 8A, as shown in FIG. 7. If photographing is carried out by manipulating the photographing switch 5B under this state, the mesh 61h is changed from the low brightness to the high brightness, and it is displayed on the screen 8A that photographing of the portion Er8 has been carried out. The meshes 61a and 61h having the high brightness as a result of execution of photographing are shown shaded in FIG. 7. At the same time, the portion Er8 is recorded in the still video recorder 7. When each of the photographed portions Er1 to Er9 is recorded in the still video recorder 7, the control unit 9 records the position information of portions to be photographed in the recorder 7 together with each of the photographed portions Er1 to Er9. In this embodiment, the same symbols Er1 to Er9 are used as the position information.

Further, it is more desirable for the recognition pattern 61 to be constructed so that a mesh corresponding to a portion is to be photographed in the next step, e.g., the mesh 61a when the light-emitting diode 51a is lit, is flickered. In other words, it is more desirable to flicker a portion that is to be photographed in the next step in contrast with a portion that has been already photographed so as to enable distinguishing between them.

Also, when the manipulation means 60 is manipulated so as to photograph the same portion again, e.g., when the light-emitting diode 51a is lit again, it suffices to flicker the central portion alone of the mesh 61a in place of the entire region of the mesh 61a. Specifically, when a portion that has been photographed is photographed again, it is desirable to display the photographed portion by a flickering fashion differing from that in the previous photographing. Further, if the number of photographs of the particular portion is displayed on the particular mesh, it is possible to obtain the merits that the number of overlapping photographs can be known, and that the ordinary flickering fashion can be employed.

Figure 8:
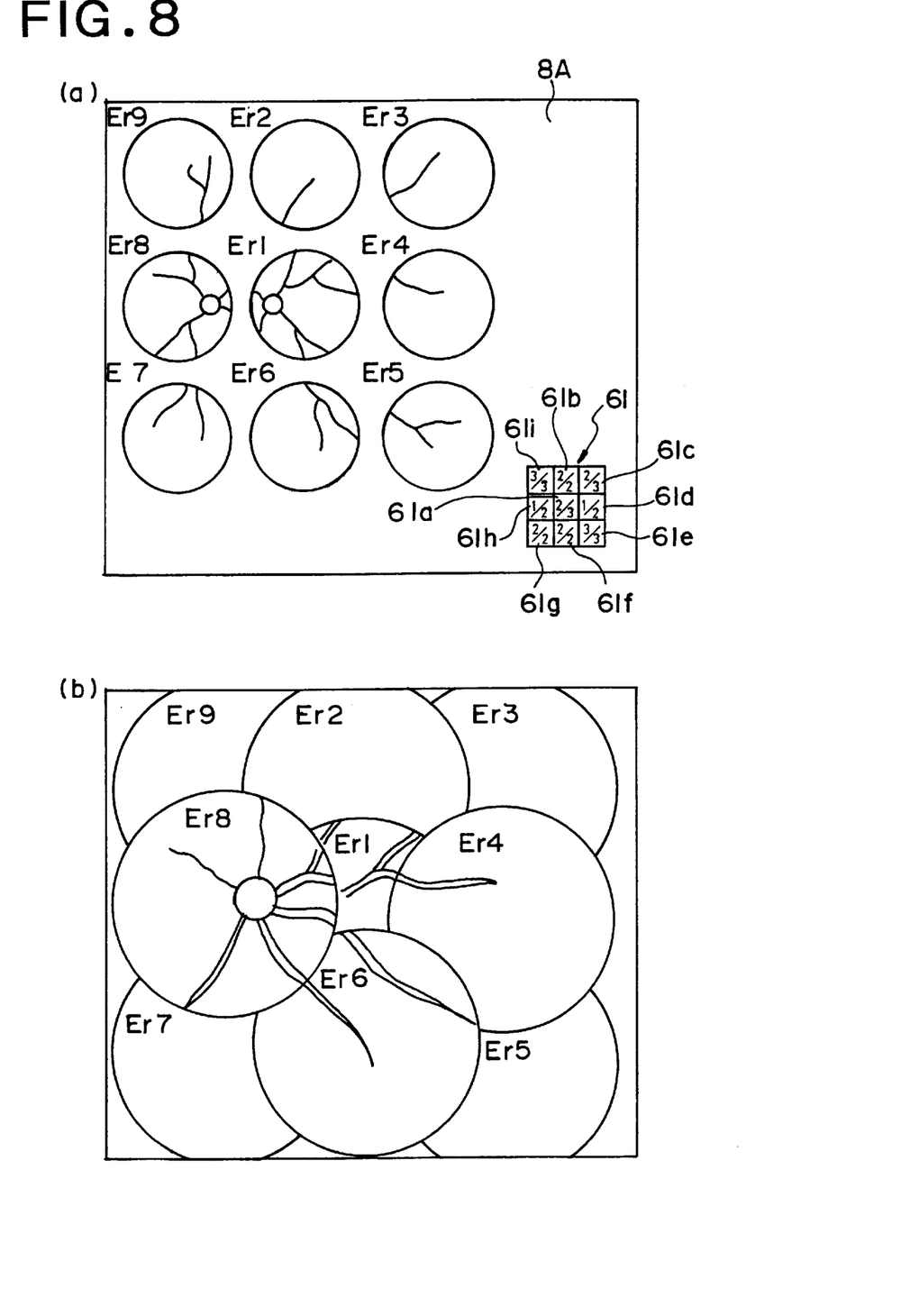

If the manipulation means 60 is manipulated in order to call out the portions Er1 to Er9 recorded in the still video recorder 7, nine partial images of the portions Er1 to Er9 are displayed on the screen 8A, as shown in FIG. 8(a). These nine partial images are displayed on the monitor in a manner to conform to the arrangement of the recognition pattern. If one of the small screens on which these partial images are displayed is clicked by the mouse, the clicked partial image is displayed in a magnified fashion over the entire screen. Also, it is possible to display a panoramic image of the portions Er1 to Er9 recorded in the still video recorder 7 in conformity with the information on the eye fixing positions by a known image processing means as shown in FIG. 8(b).

Figure 9:
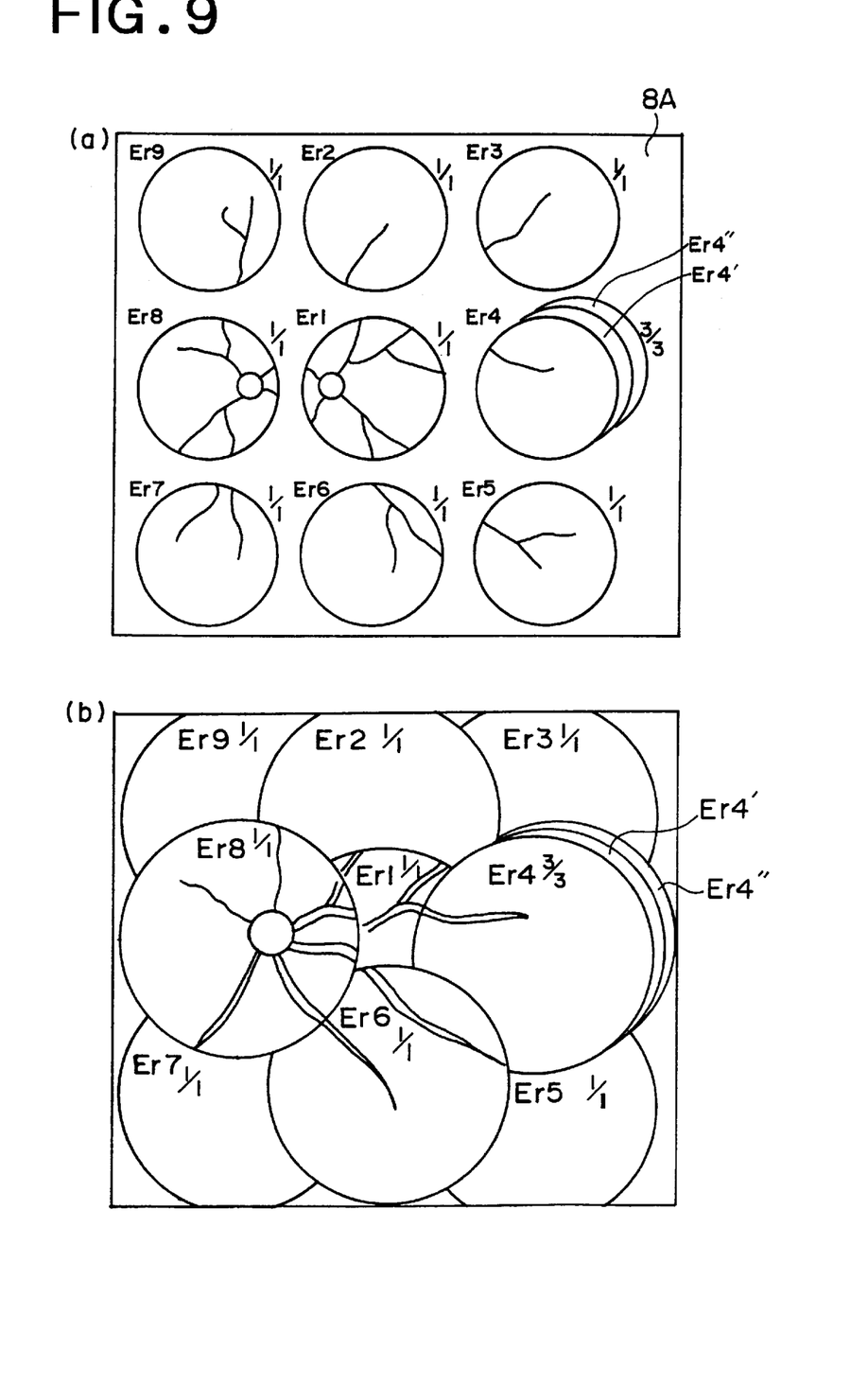

It should be noted that, where the same portion is photographed a plurality of times, the image obtained by the last photographing generally has the best photographing condition and, thus, it is desirable to use the photograph obtained by the last photographing as the recording image to be displayed. In this case, it is possible to change the order of preference of the overlapping record images by manipulating the manipulation means 60, e.g., by clicking the mouse. For example, the recorded image hidden in the back can be displayed on the screen, and the recorded image displayed on the screen can be hidden in the back. It is also possible to display the recorded image in a manner to overlap with the nine partial images shown in FIGS. 8(a), 9(a) or with the panoramic image shown in FIGS. 8(b), 9(b). In FIG. 8(a), the number of taken photographs is displayed in each mesh of the recognition pattern 61 as a denominator, and the order of photographing of the portions displayed on the screen 8A is displayed in each mesh as a numerator. In FIG. 9(a), the images of the photographed portions are alone displayed on the screen 8A without displaying the recognition pattern 61, and the numbers of photographs and the orders of displayed images of the photographed portions are displayed on the right side in the form of fractions. Since the recognition pattern 61 is not displayed in the example shown in FIG. 9(a), the screen 8A can be broadened to make the displayed images of the photographed portions larger than those in FIG. 8(a). In FIG. 9(b), the number of photographs and the order of displayed images of the photographed portions are displayed within each screen of the panoramic image in the form of a fraction. In FIGS. 9(a) and 9(b), the images of the photographed portions that are photographed a plurality of times are displayed so as to deviate from each other. However, if a screen is made definite by the manipulation means such as mouse, the images of the photographed portions that are displayed on the back side so as to deviate from each other are deleted. Thereafter, it is possible to set again the instrument to bring the images of the photographed portions hidden on the back surface onto the front surface. Incidentally, it is possible to display the panoramic image as shown in FIG. 9(b) without taking procedures to display first the images of the photographed portions side by side as shown in FIG. 9(a), and then changing into the screen as shown in FIG. 9(b).

Figure 10:
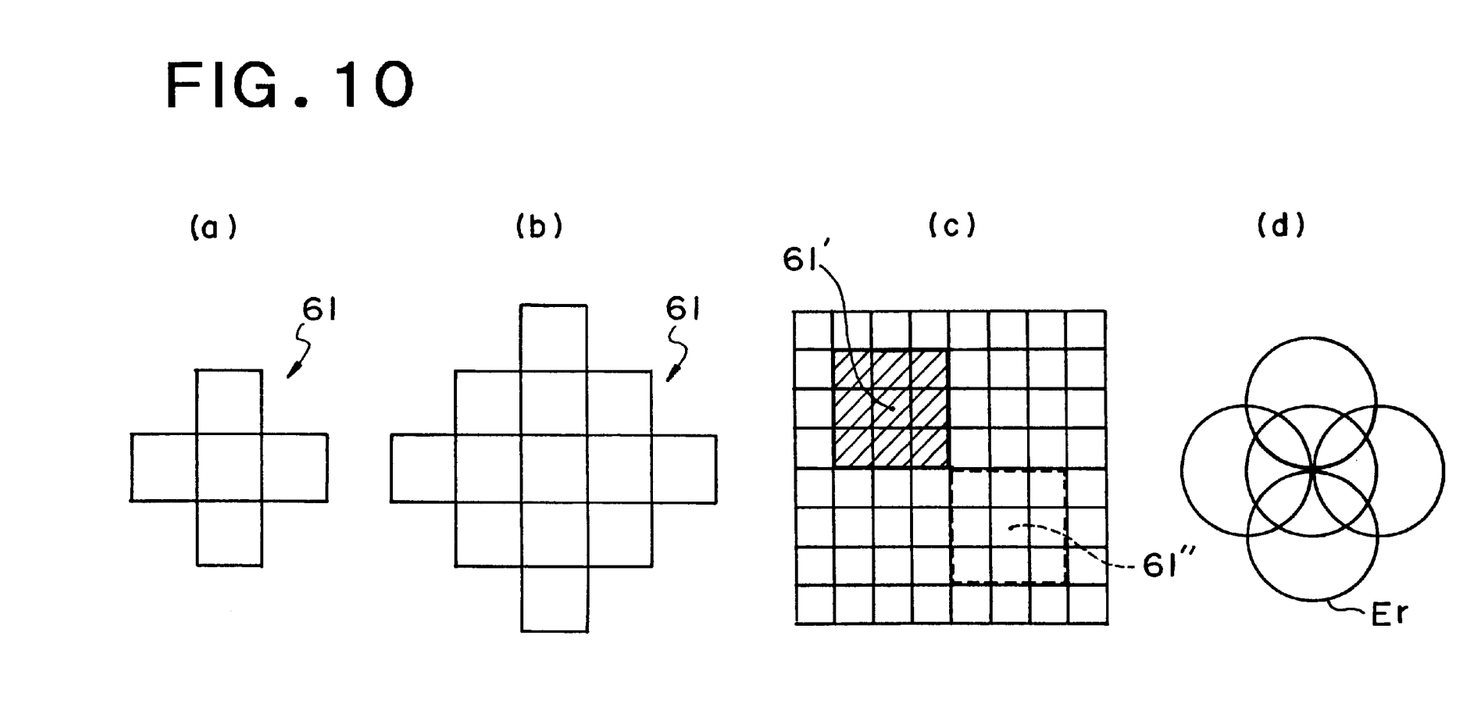

Since the portions required for the photographing depend on the purpose of photographing and the kind of diseases, the number and sites of portions of the recognition pattern can be arbitrarily selected and changed by the mouse and the like. Further, it is more convenient to store the numbers and sites of portions of the recognition patterns of the typical photographing patterns in a memory means (not shown) of the photographic instrument for ophthalmology and to select the required combination of number and sites from the stored data. For example, it is possible for the recognition pattern 61 to be in the shape of a cross (+), as shown in FIG. 10(*a*). It is also possible for the recognition pattern to be based on a square configuration consisting of nine square meshes (3 square meshes×3 square meshes) and four additional meshes each positioned adjacent to the central mesh of each of the four sides of the square configuration, as shown in FIG. 10(*b*). Further, it is possible to use a square configuration consisting of 64 square meshes (8 square meshes×8 square meshes), as shown in FIG. 10(*c*). In this case, a recognition pattern 61' for the standard photography is denoted by a thick frame. If a mesh 61' of the recognition pattern for the standard photography is designated, the central portion of the fundus can be photographed and eight photographs can be taken in the fundus portions around the central portion of the fundus. When there is a disease in the fundus, another mesh, e.g., a mesh 61", is designated so as to eight photographs of the fundus portions around the fundus portion corresponding to the mesh 61". Of course, the instrument is not limited to the embodiment exemplified above.

FIG. 10(*d*) shows portions of the fundus Er corresponding to the recognition pattern shown in FIG. 10(*a*). Since the number of portions to be photographed is small, it is possible to enlarge the overlapping portion of the fundus.

Figure 11:
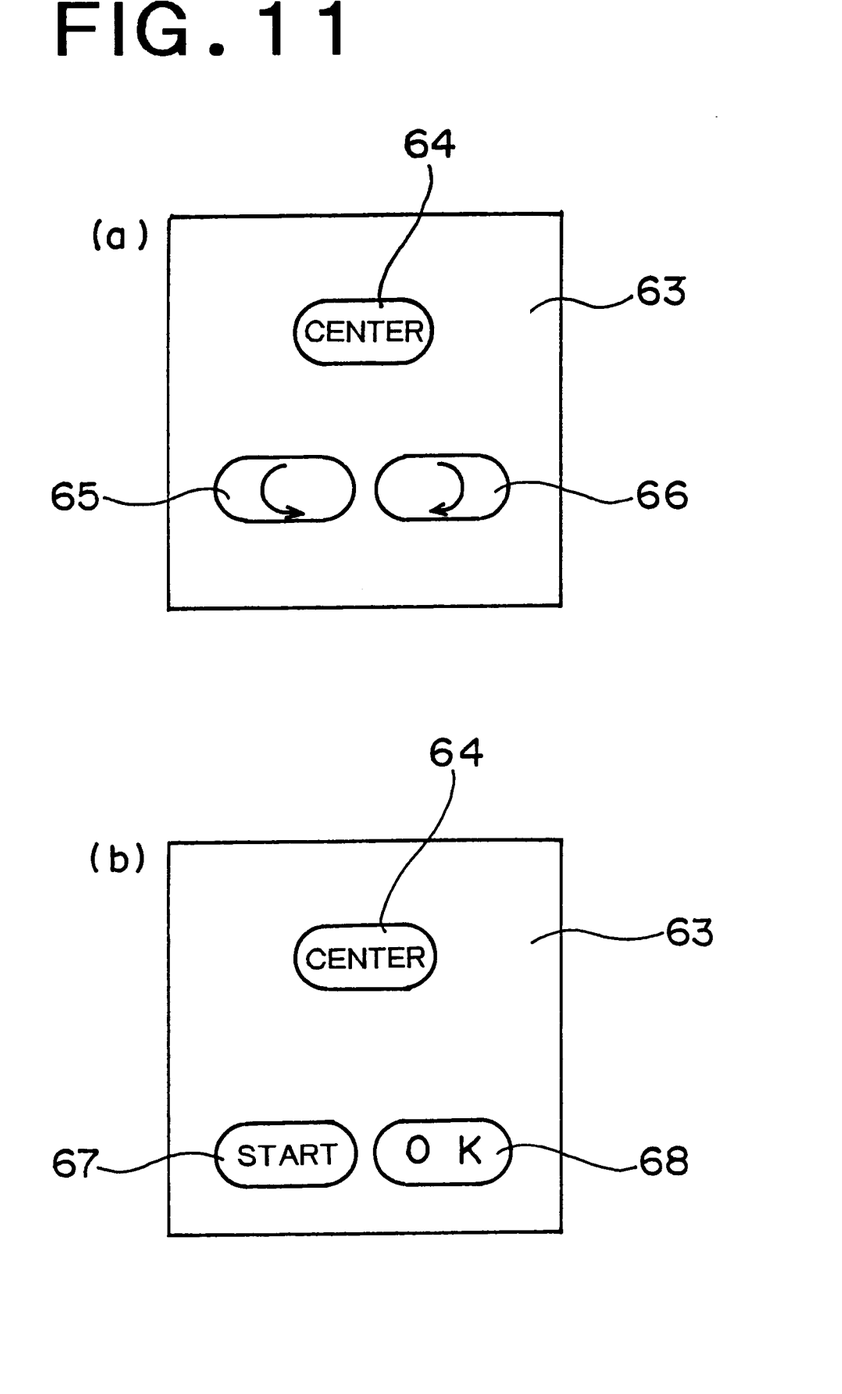
FIG. 11 shows a manipulation panel for controlling the lighting of a fixation lamp, wherein FIG. 11(a) covers a case where a switch for lighting the fixation lamp in a clockwise direction and another switch for lighting the fixation lamp in a counterclockwise direction are arranged in the photographing of the peripheral portion, and FIG. 11(b) exemplifies a switch dedicated for lighting a fixation lamp for the peripheral photography when a peripheral portion is photographed.

Further, a manipulation switch panel 63 for controlling the lighting of the eye fixing lamp shown in FIG. 11(*a*) is arranged in a predetermined position of the instrument body 1C. A center lighting switch 64, a counterclockwise lighting switch 65 and a clockwise lighting switch 66 are arranged in the manipulation switch panel 63. The central portion Er1 of the fundus is photographed by lighting the center lighting switch 64. When the fundus portions Er2 and Er3 to Er9 are photographed successively in the clockwise direction starting with the central portion, the clockwise lighting switch 66 is successively pressed so as to successively change the eye fixing lamps to be lit and, thus, to photograph the fundus images of the peripheral portions. Further, when the fundus portions Er2 and Er3 to Er9 are photographed successively in the counterclockwise direction starting with the central portion, the counterclockwise lighting switch 65 is successively pressed so as to successively change the eye fixing lamps to be lit and, thus, to photograph the fundus images of the peripheral portions. In this case, if the same fundus portion is photographed again, the same fundus portion can be photographed again by manipulating the photographing switch 5B in place of pressing the lighting switches. Also, when it is intended to photograph the central fundus portion again, it suffices that the center lighting switch 64 is pressed again so as to light the central eye fixing lamp.

Further, where the fundus portion of the other eye is to be photographed, it is convenient to use a known switch that is interlocked with the horizontal movement of the rest 1B so as to be turned on and off, thereby the central eye fixing lamp is automatically lighted.

It is also possible to arrange a start switch 67 and an OK switch 68 in the manipulation panel switch 63 as shown in FIG. 11(*b*) in place of the counterclockwise lighting switch 65 and the clockwise lighting switch 66, respectively, shown in FIG. 11(*a*). In this case, the eye fixing lamps for the peripheral photographing can be lit by pressing the start switch 67, and the eye fixing lamps to be lit are successively changed by manipulating the OK switch 68 so as to successively photograph the peripheral fundus portions.

In this embodiment, the meshes 61*a* to 61*i* are used for recognizing the photographing end points and the positional relationship of the photographed portions. Alternatively, it is possible to perform the display by using dots in place of the meshes. It is also possible to perform the display by changing the color or by employing a flickering display. Further, it is possible to manipulate the manipulation means 60 to move the recognition pattern 61 to a position on the screen where the recognition pattern 61 can be observed easily.

Embodiment 2

Figure 12:
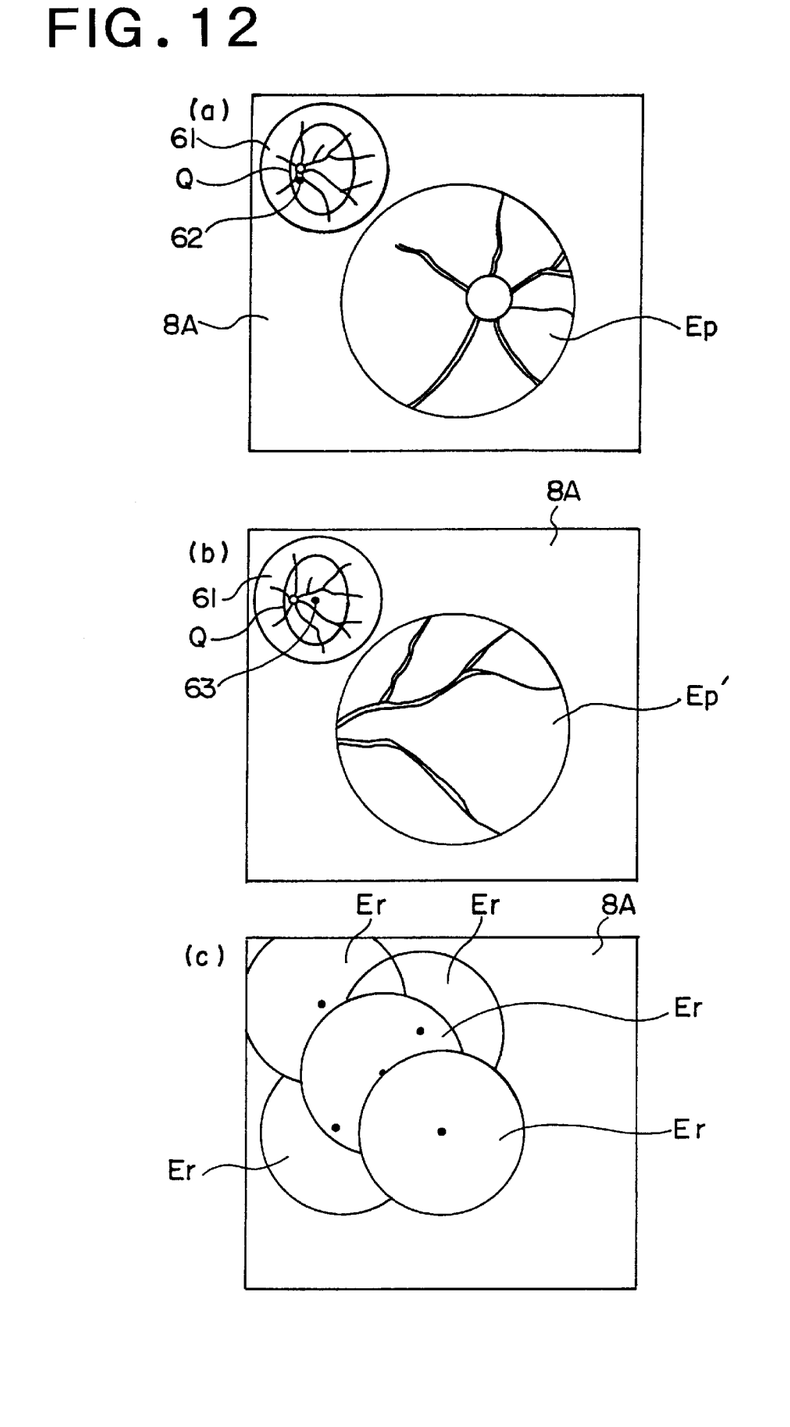

In this embodiment, a fundus image or a schematic fundus image is displayed on the screen 8A in a reduced fashion as the recognition pattern 61 as shown in FIGS. 12(*a*) and 12(*b*) so as to permit the position of an optional photographed portion relative to the entire fundus Er to be recognized when the optional photographed portion is photographed by guiding the eye to be examined by the external eye fixing lamp 4. To be more specific, the portion of the recognition pattern 61 corresponding to the portion where an alignment image is displayed is designated by manipulating the manipulation means 60, so as to record the specific photographed portion of the fundus together with the information concerning which portion of the entire fundus Er was photographed. In FIG. 12(*a*), a fundus portion Ep including the papilla portion is displayed on the screen 8A as an alignment image. In this case, a portion 62 in the vicinity of the papilla of the recognition pattern 61 is designated after photographing the portion Ep. Thus, the portion 62 is recorded together with the portion Ep in the still video recorder 7 as the information on the photographed portion, and the fundus portion Ep is related to the information concerning the position of the fundus Er. FIG. 12(*b*) shows that a fundus portion Ep' in the vicinity of the papilla on the right side thereof is displayed on the screen 8A as an alignment image. In this case, a region 63 on the right side of the portion 62 in the recognition pattern 61 is designated. As a result, the region 63 is recorded together with the fundus portion Ep' in the still video recorder 7 as the photographed portion information, and the fundus portion Ep' is related to the position of the fundus Er.

Accordingly, it is possible to confirm promptly which portion of the entire of the fundus Er the recorded fundus portion corresponds to, if the recognition pattern 61 is displayed simultaneously on the screen 8A together with the photographed fundus portion when the photographed fundus portion is displayed on the screen 8A by manipulating the manipulation means 60. According to this embodiment of the present invention, the degree of freedom of selection of the portions of the fundus to be photographed is increased.

For example, in the case of diabetes, the disease is said to proceed from the periphery of the fundus of an eye. When the peripheral portion of the fundus, which cannot be photographed satisfactory by an inner eye fixation, is photographed by using an outer eye fixation, the present invention produces a merit that a panoramic image can be prepared easily.

To be more specific, since the number of blood vessels and the density of blood vessels are decreased in the periphery of the fundus to make it difficult to deal with the situation by the naked eye. Therefore, it is difficult to recognize the mutual positions of the fundus portions by the naked eye. According to embodiment 2 of the present invention, however, the center (eye fixation center Z) of each of the photographed portions is designated by the mouse. Then, the distance between the centers of the photographed portions (partial images) is obtained by calculation so as to specify the relative positions of the photographed portions and is displayed on the screen 8A as a panoramic image as shown in FIG. 12(*c*). In this case, the panoramic image can be prepared easily because the mutual positional relationship among the fundus portions can be grasped easily. FIG. 12(*c*) shows the state that the examiner judged that a disease is likely to be present in the upper left portion of the fundus and the examiner performed concentrated photographing of the fundus portions in the periphery of the upper left portion. The examiner judges the mutual positional relationship based on the displayed partial images Er so as to finally prepare a panoramic image.

In this embodiment, the photographic instrument for ophthalmology is constituted so that when an eye to be examined is photographed, a portion to be photographed is displayed as an alignment image and, at the same time, the recognition pattern is also displayed. Alternatively, the photographic instrument for ophthalmology may be constituted so that after photographing, an image displayed on the screen 8A is switched from the alignment image to an input screen of the photographed portion on which the recognition pattern 61 alone is displayed.

It should be noted that, in a fundus camera having an automatic focusing device incorporated therein, when the peripheral portion is photographed, it may be sometimes impossible to detect a focused state because the peripheral portion exceeds an operation scope of the automatic focusing device. Therefore, it is desirable to display the normal operation scope of the automatic focusing device together with the recognition pattern 61. A symbol Q in each of FIGS. 12(*a*) and 12(*b*) denotes the limit of the normal operation of the automatic focusing device. In the inside of the operation limit Q, the automatic focusing device operates normally, making it possible to photograph the fundus image that is automatically put in focus. However, in the outside of the operation limit Q, the automatic focusing device fails to operate normally. Therefore, when the peripheral image outside the operation limit Q is photographed, the photographer manually adjusts the focus to photograph the fundus image.

Embodiment 3

Figure 13:
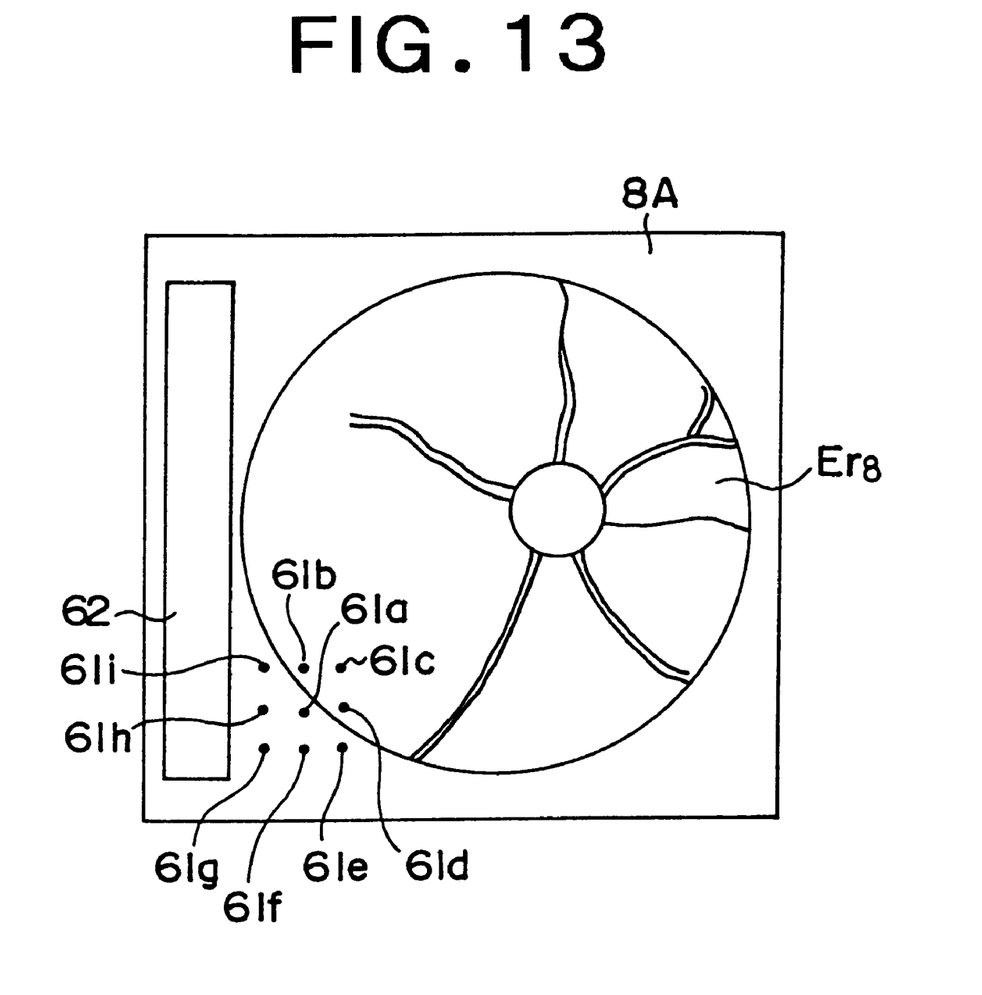
FIG. 13 is an explanatory view showing a third embodiment of the present invention and shows a state that a recognition pattern is displayed by dots.

In this embodiment, the recognition pattern 61 is displayed by nine dots 61*a* to 61*i* arranged so as to form a matrix, as shown in FIG. 13, and some of these dots are superposed on a portion to be photographed in the lower left portion of the screen. In FIG. 13, a counter 62 for displaying the ID number, name, etc. of the patient is displayed on the left side of the screen.

In the embodiments described above, the photographic instrument for ophthalmology is constituted so that a recognition pattern is displayed on the screen. However, the present invention is not limited to the particular embodiments. Specifically, it is possible to superpose a recognition pattern on the fundus image within a field of vision of a finder to display the recognition pattern. In this case, an examiner can photograph the fundus image while looking into the finder. Also, the embodiments described above are directed to the photography of the fundus. However, the present invention can also be applied to the photography of the corneal endothelium and the cornea cross section.

The present invention is not limited to the embodiments described above and includes modifications given below.

Specifically, it is possible to provide a re-photographing switch in preparation for the failure in the photography of the fundus portion. In such a case, the same eye fixing lamp as one that was lit in the failed photography is lit by the re-photographing switch so as to be able to photograph again the same fundus portion. In this case, it may be possible that the failure image stored in the memory means is erased, and that the partial image photographed by the re-photographing switch is stored in the same memory region of the memory means.

Effect of the Invention:

The particular construction of the present invention described above makes it possible to easily recognize portions to be photographed of an eye to be examined and photographed portions of the eye, and thus the mutual positional relationship of the photographed images can be easily recognized.

What is claimed is:

1. A photographic instrument for ophthalmology, comprising display means for displaying portions to be photographed each as a part of an entire of an eye to be examined as alignment images together with a recognition pattern for recognizing positions of the portions to be photographed relative to the entire of the eye to be examined when the eye to be examined is photographed.

2. A photographic instrument for ophthalmology according to claim 1, wherein a plurality of combinations of numbers and sites of said portions are previously stored in memory means of the photographic instrument for ophthalmology and the numbers and sites can be arbitrarily selected from among the stored combinations.

3. A photographic instrument for ophthalmology according to claim 1, wherein said recognition pattern is displayed so that a portion that has been photographed can be distinguished from a portion that has not been photographed yet.

4. A photographic instrument for ophthalmology according to claim 1, wherein a portion that is to be photographed in a next step is displayed in said recognition pattern.

5. A photographic instrument for ophthalmology according to claim 1, wherein said recognition pattern is displayed as another pattern when the same portion is photographed again.

6. A photographic instrument for ophthalmology according to claim 1, wherein said recognition pattern displays a number of photographs to make it possible to know the number of the photographs of a portion that has been photographed.

7. An ophthalmologic photographic instrument, comprising:

display means for displaying a recognition pattern for permitting a position of a photographed portion to be recognized relative to an entire of an eye to be examined when said eye to be examined is photographed or after said eye is photographed; and recording means for recording an image of the photographed portion as well as positional information on the photographed portion that indicates the position of the photographed portion relative to the entire of a fundus while allowing the image of the photographed portion to be related to the entire of a fundus by designating a position in the recognition pattern displayed on a screen.

8. A photographic instrument for ophthalmology according to claim 7, wherein the photographed portion of said eye to be examined is its fundus, corneal endothelium or cornea cross section.

9. A photographic instrument for ophthalmology according to claim 7, wherein the photographed portion of said eye to be examined is its fundus and said recognition pattern is a fundus image or a schematic fundus image.

10. A photographic instrument for ophthalmology, wherein, when a portion to be photographed is displayed in a way of a panoramic display, each partial image is displayed on a screen in a manner to correspond to information on an eye fixing position.

* * * * *